United States Patent
Kooh et al.

(10) Patent No.: US 10,543,245 B2
(45) Date of Patent: *Jan. 28, 2020

(54) COMPOSITION FOR PREVENTING OR TREATING HYPERLIPIDEMIA

(71) Applicant: HAWON PHARM. CORPORATION, Gyeonggi-do (KR)

(72) Inventors: Dae-ho Kooh, Seoul (KR); Sung-Kew Kim, Busan (KR); Young-Chan Baik, Seoul (KR); Young-Bong Shin, Seoul (KR); Myoung Seok Kim, Jeollanam-do (KR)

(73) Assignee: HAWON PHARM. CORPORATION, Gyeonggi-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/512,620

(22) Filed: Jul. 16, 2019

(65) Prior Publication Data

US 2019/0336557 A1 Nov. 7, 2019

Related U.S. Application Data

(62) Division of application No. 15/507,520, filed as application No. PCT/KR2015/005318 on May 27, 2015.

(30) Foreign Application Priority Data

Aug. 29, 2014 (KR) .......................... 10-2014-0113807

(51) Int. Cl.
*A61K 36/734* (2006.01)
*A61K 36/236* (2006.01)
*A61K 36/704* (2006.01)
*A61K 36/537* (2006.01)

(52) U.S. Cl.
CPC .......... *A61K 36/734* (2013.01); *A61K 36/236* (2013.01); *A61K 36/537* (2013.01); *A61K 36/704* (2013.01)

(58) Field of Classification Search
None
See application file for complete search history.

(56) References Cited

PUBLICATIONS

U.S. Appl. No. 15/507,520, filed Feb. 2017, Kooh; Dae-Ho.*
U.S. Appl. No. 16/512,648, filed Jul. 2019, Kooh; Dae-Ho.*
Lee, et al., Korean J. Orient. Int. Med., 29:432. (Year: 2008).*
Xie, et al., Journal of Ethnopharmacology, 140:34. (Year: 2012).*

* cited by examiner

*Primary Examiner* — Michael Barker
(74) *Attorney, Agent, or Firm* — The PL Law Group, PLLC

(57) ABSTRACT

A method for preventing or treating hyperlipidemia includes administrating a composition consisting of a *Salvia miltiorrhiza* extract, a *Crataegus pinnatifida* extract, a *Polygonum multiflorum* extract, and a *Ligusticum chuanxiong* extract to a subject in need thereof. The composition may reduce an amounts of serum cholesterol and LDL-cholesterol and increase an amount of HDL-cholesterol, significantly reduce an amount of serum triglyceride compared with existing statin-based drugs, thereby exhibiting prophylactic and therapeutic effects of hyperlipidemia with various symptoms even without the co-administration of other drugs; and reduce an amounts of hepatic to cholesterol and triglyceride, thereby exhibiting an effect of inhibiting fatty liver.

2 Claims, 1 Drawing Sheet

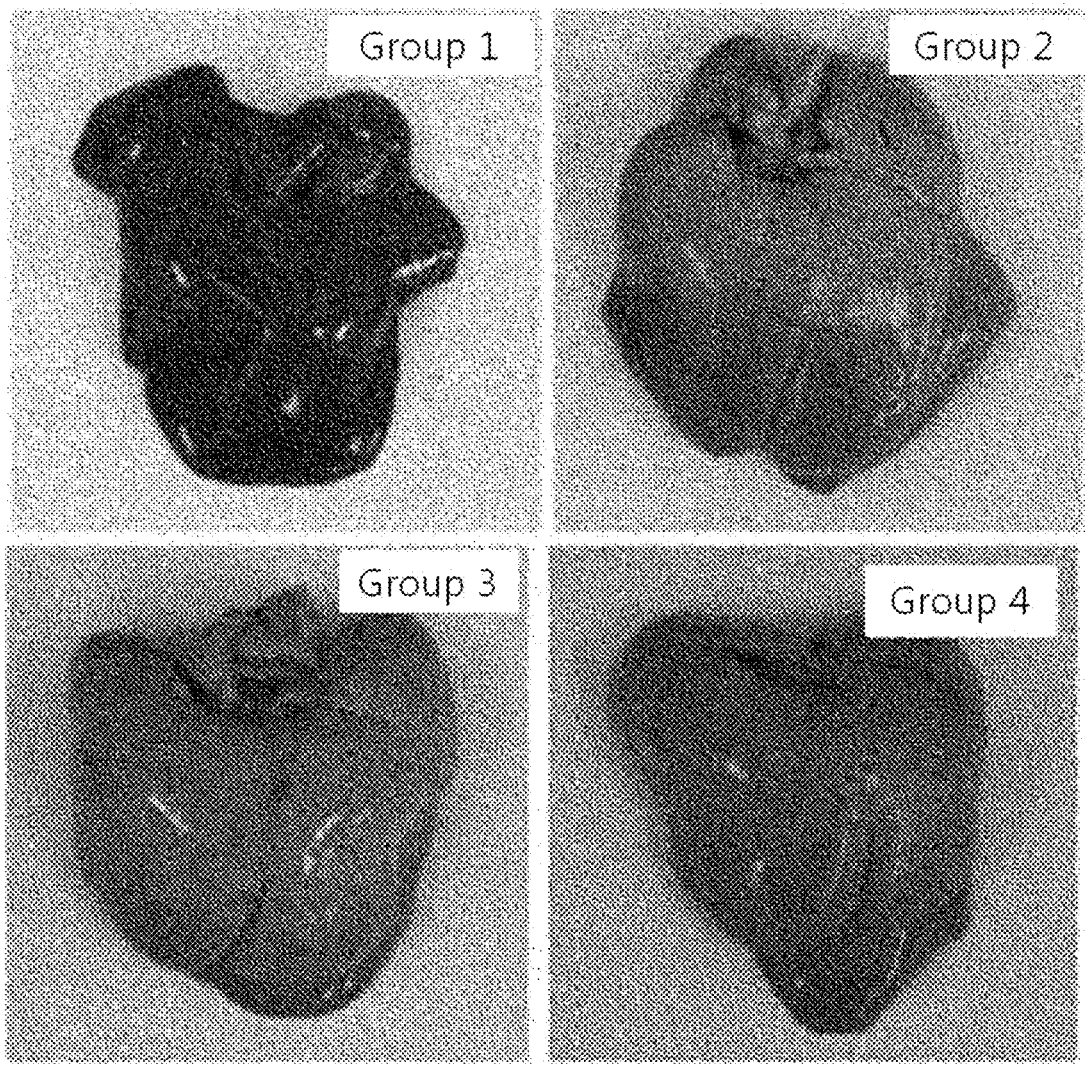

COMPOSITION FOR PREVENTING OR TREATING HYPERLIPIDEMIA

CROSS REFERENCE TO RELATED APPLICATIONS AND CLAIM OF PRIORITY

This application is a divisional application of application Ser. No. 15/507,520, filed on Feb. 28, 2017, which is a National Stage entry under 35 U.S.C. § 371 of International Application No. PCT/KR2015/005318, filed May 27, 2015, which claims priority to the benefit of Korean Patent Application No. 10-2014-0113807 filed in the Korean Intellectual Property Office on Aug. 29, 2014, the entire contents of which are incorporated herein by reference.

BACKGROUND

Technical Field

The present invention relates to a pharmaceutical composition for preventing or treating hyperlipidemia.

2. Background Art

In recent years, metabolic diseases such as hyperlipidemia are increasing due to the increase of fat intake and lack of exercise by economic growth, a habit of overeating, and westernization in Korea.

Hyperlipidemia is not usually symptomatic in itself, but if a large amount of fatty substances is present in the blood, they may cling to the blood vessel wall and cause arteriosclerosis, which eventually may lead to coronary heart disease, cerebrovascular disease, peripheral vascular occlusion, and the like (E. Falk et al., Circulation 92, 657-671, 1995). In addition, such excessive fatty substances as described above accumulate in the liver tissue, which may cause fatty liver.

On the other hand, as a method for decreasing a lipid concentration in blood, diet, exercise and drug therapies are recommended to suppress the intake of foods containing a lot of cholesterol and saturated fatty acids and reduce caloric intake. However, such diet and exercise therapies are difficult to manage and practice strictly, and their effects are often limited.

To date, statins, known as HMG-CoA reductase inhibitors and known to have a great effect in the treatment of hyperlipidemia, have been shown to reduce the production of cholesterol by controlling the rate determining step of a reaction through which cholesterol where HMG-CoA reductase acts during lipid metabolism is produced. However, a statin is a drug metabolized by hepatic p450dp, which can cause liver toxicity by inducing an interaction with numerous drugs, and can cause side effects such as digestive disorders, headaches, fatigue, muscle aches, joint pain, and the like.

Accordingly, research is being conducted on natural products which can prevent or treat hyperlipidemia, arteriosclerosis, and fatty liver by reducing an excessive lipid concentration in blood, and which are also safe for humans and have no side effects.

Korean Laid-Open Patent Publication No. 2010-0089910 discloses a composition for preventing and treating hyperlipidemia, which comprises a mixed herbal medicine extract as an active ingredient.

SUMMARY

It is an aspect of the present disclosure to provide a pharmaceutical composition for preventing or treating hyperlipidemia which has excellent effects even without side effects.

It is another aspect of the present disclosure to provide a pharmaceutical composition for the prevention or treatment of hyperlipidemia which does not require the co-administration of other drugs by significantly reducing the amount of triglycerides in blood as compared with conventional statin-based drugs, as well as reducing the amount of LDL-cholesterol and increasing the amount of HDL-cholesterol.

It is a still another aspect of the present disclosure to provide a pharmaceutical composition for preventing or treating hyperlipidemia which further has a fatty liver inhibiting effect.

One aspect of the present disclosure provides a pharmaceutical composition for preventing or treating hyperlipidemia, including a *Salvia miltiorrhiza* extract, a *Crataegus pinnatifida* extract, a *Polygonum multiflorum* extract, and a *Ligusticum chuanxiong* extract.

According to some embodiments of the present disclosure, the composition may further have a fatty liver inhibiting effect.

According to some embodiments of the present disclosure, the *Salvia miltiorrhiza* extract, the *Crataegus pinnatifida* extract, the *Polygonum multiflorum* extract, and the *Ligusticum chuanxiong* extract may be contained in a weight ratio of 1.5 to 2:3.5 to 4:2.5 to 3:0.5 to 1.

According to some embodiments of the present disclosure, the *Salvia miltiorrhiza* extract, the *Crataegus pinnatifida* extract, the *Polygonum multiflorum* extract, and the *Ligusticum chuanxiong* extract may be contained in a weight ratio of 1.5 to 2:2.6 to 3:0.4 to 1:1.4 to 2.

According to some embodiments of the present disclosure, the *Salvia miltiorrhiza* extract, the *Crataegus pinnatifida* extract, the *Polygonum multiflorum* extract, and the *Ligusticum chuanxiong* extract may be contained in a weight ratio of 2.5 to 3.5:4 to 5:2.5 to 3.5:1 to 2.

Another aspect of the present disclosure provides a health functional food for the improvement of hyperlipidemia, including a *Salvia miltiorrhiza* extract, a *Crataegus pinnatifida* extract, a *Polygonum multiflorum* extract, and a *Ligusticum chuanxiong* extract.

One or more embodiments of the present disclosure has an effect of preventing and treating hyperlipidemia by reducing the amount of cholesterol and LDL-cholesterol and increasing the amount of HDL-cholesterol in blood.

One or more embodiments of the present disclosure significantly reduces the amount of triglycerides in blood as compared with conventional statin-based drugs, and thus exhibits excellent pharmacological effects on various symptoms of hyperlipidemia even without the co-administration of other drugs.

One or more embodiments of the can reduce the amount of hepatic cholesterol and triglycerides to suppress fatty liver.

In addition, since the present disclosure is made up of herbal medicine extracts, side effects that occur during the use of conventional statin-based drugs for treating hyperlipidemia do not occur.

BRIEF DESCRIPTION OF THE DRAWINGS

FIG. 1 illustrates liver tissues of: SD rats with a normal diet (Group 1) and a high cholesterol diet (Group 2), and SD rats treated with a control drug (Group 3) and a pharmaceutical composition of Example 1 (Group 4) after a high cholesterol diet.

DETAILED DESCRIPTION

Hereinafter, exemplary embodiments of the present disclosure will be described in detail. However, the present disclosure is not limited to the exemplary embodiments disclosed below, but can be implemented in various forms. The following exemplary embodiments are described in order to enable those of ordinary skill in the art to embody and practice the invention.

One aspect of the present disclosure is a pharmaceutical composition for preventing or treating hyperlipidemia, wherein the pharmaceutical composition comprises a *Salvia miltiorrhiza* extract, a *Crataegus pinnatifida* extract, a *Polygonum multiflorum* extract, and a *Ligusticum chuanxiong* extract, thereby reducing the amounts of cholesterol and LDL-cholesterol and increasing the amount of HDL-cholesterol in blood; significantly reduces the amount of triglycerides in blood compared with conventional statin-based drugs, thereby exhibiting prophylactic and therapeutic effects on various symptoms of hyperlipidemia even without the co-administration of other drugs; and reduces the amounts of hepatic cholesterol and triglycerides, thereby exhibiting an effect of inhibiting fatty liver.

Hereinafter, the present disclosure will be described in detail.

<Composition>

The pharmaceutical composition of the present disclosure includes a *Salvia miltiorrhiza* extract, a *Crataegus pinnatifida* extract, a *Polygonum multiflorum* extract, and a *Ligusticum chuanxiong* extract.

The present disclosure has an effect of preventing and treating hyperlipidemia by reducing the amount of cholesterol, triglycerides and LDL-cholesterol, and increasing the amount of HDL-cholesterol in blood.

In the case of hyperlipidemia, there are various symptoms such as an increase in the amount of cholesterol and LDL-cholesterol, or an increase in the amount of triglycerides. However, the conventionally used statin-based treatment for hyperlipidemia mainly has an effect of reducing the amount of LDL-cholesterol. Therefore, there is a problem in that the drug efficacy is lowered in patients with hyperlipidemia, in which the amount of triglycerides is large, and thereby other drugs should be used in combination.

However, the pharmaceutical composition of the present disclosure not only reduces the amount of cholesterol and LDL-cholesterol but also increases the amount of HDL-cholesterol and significantly reduces the amount of triglycerides in blood to a level similar to that of a normal group, thereby exhibiting excellent pharmacological effects on various symptoms of hyperlipidemia even without the co-administration of other drugs.

In addition, according to the present disclosure, the amount of total cholesterol and triglycerides in the liver can be reduced to inhibit fatty liver, and the herbal medicine extracts can prevent the side effects of the conventionally used statin-based treatment drugs of hyperlipidemia.

As used herein, hyperlipidemia refers to a state in which fats such as free cholesterol, cholesterol esters, phospholipids, triglycerides, and the like are abnormally increased in blood. This means that excessive fatty substances are present in the blood and accumulate on the blood vessel wall to cause inflammation, resulting in cardiovascular diseases. In recent years, an abnormal amount of lipids in the blood is also defined as dyslipidemia.

In addition, the fatty liver refers to a state in which the proportion of fats in the liver weight exceeds 5%, and may be caused not only by excessive fat intake but also by alcohol intake.

As used herein, the *Salvia miltiorrhiza* (scientific name; also called "dansam" in Korea) is a perennial plant belonging to the family Lamiaceae, and the genus *Salvia*. The *Salvia miltiorrhiza* has excellent efficacy against eosinophilia, bruises, neuralgia, arthritis, and especially gynecological diseases and menstrual disorders. The root is used as a medicinal part.

As used herein, the *Crataegus pinnatifida* is a mature fruit of the hawthorn tree belonging to the family Rosaceae and is a scientific name for hawthorn fruit. The ripe fruit is used for medicinal purposes, and it promotes digestion and has cardiotonic activity. Further, it is used for abdominal pain, vomiting, diarrhea, gastric hyperalgesia, chronic enteritis, and the like.

As used herein, the *Polygonum multiflorum* root (scientific name) is a herbaceous perennial vine that belongs to the family Polygonaceae. The round root is used as a medicinal part, and it has an effect of a tonic, nourishing of blood, strengthening of vital essence and energy, elimination of epilepsy and swelling. Further, it is used to treat gynecological diseases or abdominal cavity diseases, darken hair, and improve a complexion.

As used herein, the *Ligusticum chuanxiong* belongs to the order Apiales, the family Apiaceae, the genus *Ligusticum*, and its scientific name is Cnidium Rhizome. The root stalk is used as a medicinal part. In the herbal remedy, the root stalk is effective for calmness, pain, and a tonic, and therefore used for headaches, anemia, gynecological diseases, and the like.

According to one embodiment of the present disclosure, the *Salvia miltiorrhiza* extract, the *Crataegus pinnatifida* extract, the *Polygonum multiflorum* extract, and the *Ligusticum chuanxiong* extract may be contained in a weight ratio of 1.5 to 2:3.5 to 4:2.5 to 3:0.5 to 1. According to another embodiment of the present disclosure, the *Salvia miltiorrhiza* extract, the *Crataegus pinnatifida* extract, the *Polygonum multiflorum* extract, and the *Ligusticum chuanxiong* extract may be contained in a weight ratio of 1.5 to 2:2.6 to 3:0.4 to 1:1.4 to 2. According to still another embodiment of the present disclosure, the *Salvia miltiorrhiza* extract, the *Crataegus pinnatifida* extract, the *Polygonum multiflorum* extract, and the *Ligusticum chuanxiong* extract may be contained in a weight ratio of 2.5 to 3.5:4 to 5:2.5 to 3.5:1 to 2. When the composition of the present disclosure contains each of the extracts in the above respective weight ratios, the drug efficacy against hyperlipidemia can be maximized.

The present disclosure can effectively combine such herbal medicines known to have few side effects on the human body, and extract and concentrate them with ethanol to maximize the concentration of the herbal composition. In addition, the resulting concentrate of the herbal composition may be dried to provide a powdery composition, which is convenient for dosing and carrying.

The pharmaceutical composition for preventing or treating hyperlipidemia may further include suitable carriers, excipients and diluents conventionally used in the production of pharmaceutical composition. The pharmaceutical composition for the prevention or treatment of hyperlipidemia may be formulated in the form of oral preparations such as powders, granules, tablets, capsules, suspensions, emulsions, syrups, aerosols or the like, external preparations, suppositories, and sterilized injection solutions according to a conventional method. Specific examples of carriers, excipients and diluents that can be included in the composition may include, but are not limited to, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oil, and the like.

In the case of formulation, diluents or excipients such as fillers, extenders, binders, wetting agents, disintegrants, or surfactants, can usually be used.

A solid formulation for oral administration may include tablets, pills, powders, granules, capsules, and the like. Such a solid formulation may include at least one excipient such as starch, calcium carbonate, sucrose or lactose, and gelatin, in addition to the active ingredient. In addition to simple excipients, lubricants such as magnesium stearate and talc may also be included.

A liquid formulation for oral administration may include suspensions, solutions, emulsions, syrups, and the like. Various excipients such as wetting agents, sweetening agents, fragrances, preservatives and the like may be included in addition to water and liquid paraffin which are commonly employed simple diluents.

A formulation for parenteral administration may include sterilized aqueous solutions, non-aqueous solutions, suspensions, emulsions, lyophilized formulations, and suppositories. Examples of non-aqueous solutions or suspensions may include propylene glycol, polyethylene glycol, vegetable oil such as olive oil, an injectable ester such as ethyl oleate, and the like. Examples of suppository bases may include Witepsol, Macrogol, Tween 61, laurin fat, cacao butter, glycerogelatin, and the like.

The dose of the pharmaceutical composition according to the present disclosure is not particularly limited and may be appropriately selected depending on the condition and body weight of patient, the severity of disease, the drug form, and the route and period of administration. For example, the active ingredient may be administered in an amount ranging from 0.0001 to 1000 g/kg per day on a dry weight basis, or may be 0.001 to 100 g/kg per day, 0.001 to 10 g/kg per day, 0.001 to 1 g/kg per day, 0.0001 g/kg or more per day, 0.001 g/kg or more per day, 0.05 g/kg or more per day, 0.01 g/kg or more per day, or 0.005 g/kg or more per day.

The composition described herein may be administered to mammals, including livestock, humans, and the like, via a variety of routes. There is no particular limitation on the mode of administration, and specifically, it can be administered by oral, rectal or intravenous, intramuscular, subcutaneous, intra-uterine, or intracerebroventricular injections.

<Health Functional Food>

The *Salvia miltiorrhiza* extract, the *Crataegus pinnatifida* extract, the *Polygonum multiflorum* extract, and the *Ligusticum chuanxiong* extract according to the present disclosure may be added to health food for the purpose of prevention or treatment of hyperlipidemia. When the *Salvia miltiorrhiza* extract, the *Crataegus pinnatifida* extract, the *Polygonum multiflorum* extract, and the *Ligusticum chuanxiong* extract are used as a food additive, they can be used together with other food or food ingredients, and can be suitably used according to a conventional method.

The amount of the active ingredients to be mixed may suitably be determined according to their intended use (e.g., prevention, inhibition or therapeutic treatment). However, in the case of long-term ingestion intended for health and hygiene purposes or for controlling health, the amount may be below the above ranges, and, further, since the extracts of the natural products according to the present disclosure have no problems in terms of biosafety, the active ingredients may be used in an amount exceeding the above ranges. Specifically, in the case of a health food composition, it may be contained in an amount of 1 to 5% by weight of the whole food, and in the case of a health beverage composition, it may be contained in an amount of 0.02 to 10 g, and preferably 0.3 to 1 g based on 100 ml of the composition.

The health food of the present disclosure can be formulated into one selected from the group consisting of tablets, pills, dispersants, granules, powders, capsules, and liquids, and their formulation can be carried out according to a conventional method for manufacturing health foods.

There is no particular limitation on the food to which the *Salvia miltiorrhiza* extract, the *Crataegus pinnatifida* extract, the *Polygonum multiflorum* extract, and the *Ligusticum chuanxiong* extract according to the present disclosure can be added, and examples thereof include meat, sausage, bakery, chocolate, candy, snack, confectionery, pizza, noodle, gum, dairy products including ice cream, various soups, beverages, tea, drinks, alcoholic beverages, and vitamin complexes, including all health foods in a conventional sense.

Hereinafter, the present disclosure will be described in more detail by way of examples. It is to be understood by those skilled in the art that these examples are for illustrative purposes only and that the scope of the present disclosure is not limited thereby.

The present disclosure will now be described in detail with reference to the examples.

Examples

1 L of 30% ethanol was added to the compositions shown in the following Table 1, followed by hot water treatment for 4 hours, which was repeated twice. The resulting extracts were concentrated under reduced pressure and lyophilized to prepare a pharmaceutical composition of the Examples.

TABLE 1

| Classification | Ex. 1 | Ex. 2 | Ex. 3 | Ex. 4 | Ex. 5 | Ex. 6 |
|---|---|---|---|---|---|---|
| *Cinnamomum cassia* | — | — | — | — | — | — |
| *Trichosanthis Fructus* | — | — | — | — | — | — |
| *Salvia miltiorrhiza* | 20 | 22.5 | 25 | 25 | 25 | 20 |
| *Crataegus pinnatifida* | 40 | 40 | 40 | 45 | 40 | 30 |
| *Polygonum multiflorum* | 30 | 15 | 25 | 20 | 10 | 40 |
| *Citrus aurantium* | — | — | — | — | — | — |
| *Ligusticum chuanxiong* | 10 | 22.5 | 10 | 10 | 25 | 10 |
| *Allium macrostemon* | — | — | — | — | — | — |

Experimental Examples

1. Preparation Condition and Method
(1) Experimental Animals and Breeding Conditions
6-Week-old male SD rats (Sprague-Dawley rats, body weight 180-220 g) were purchased from BioLink (Eumseong, Republic of Korea) and acclimated for a week. They were formed into groups of five rats as described in Table 2 below, and solid feed (Rodent NIH031 Open Formula Auto, Zeigler Bros., USA) and a high cholesterol diet (D12451 with 1.25% cholesterol, Research Diets Inc., USA) were freely fed. Drinking water was freely supplied. A room temperature of 22.0+/−2.0° C., a relative humidity of 50.0+/−10.0%, an illumination time of 12 hours (08:00 to 20:00), and an illuminance of 150 to 300 lux were set.

TABLE 2

| Classification | Classification criteria for laboratory animals |
|---|---|
| Group 1 | Normal group - normal diet and 0.4% CMC solution |
| Group 2 | Induced group - high cholesterol diet and 0.4% CMC solution |
| Group 3 | Control group (Atorvastatin) - high cholesterol diet and 5 mg/kg (oral administration group) |
| Group 4 | High cholesterol diet and 1,000 mg/kg (oral administration group of the composition of Ex. 1) |
| Group 5 | High cholesterol diet and 1,000 mg/kg (oral administration group of the composition of Ex. 2) |
| Group 6 | High cholesterol diet and 1,000 mg/kg (oral administration group of the composition of Ex. 3) |
| Group 7 | High cholesterol diet and 1,000 mg/kg (oral administration group of the composition of Ex. 4) |
| Group 8 | High cholesterol diet and 1,000 mg/kg (oral administration group of the composition of Ex. 5) |
| Group 9 | High cholesterol diet and 1,000 mg/kg (oral administration group of the composition of Ex. 6) |

(2) Biochemical Analysis 1—Measurement of Blood Lipid

At the end of the experiment, each group was sacrificed after fasting for 12 hours. Their blood was collected from the posterior vena cava and transferred to an EDTA tube to separate the plasma. In the separated plasma, total cholesterol (TC), LDL cholesterol (LDL-c), HDL cholesterol (HDL-c) and triglycerides (TG) were measured using a biochemical kit (Asan Pharmaceutical Co., Ltd., Seoul, Republic of Korea).

The atherogenic index (AI) was calculated by the following equation (1) according to a method of Haulund et al. and the cardiac risk factor (CRF) was calculated by the following equation (2).

$$\text{Atherogenic Index (AI)} = [(TC)-(HDL\text{-}c)]/[(HDL\text{-}c)] \quad (1)$$

$$\text{Cardiac Risk Factor (CRF)} = (TC)/(HDL\text{-}c) \quad (2)$$

(3) Biochemical Analysis 2—Lipid Analysis of Liver Tissue

The total lipids in the liver were homogenized and then extracted using a Folch method. The extracted lipids were dissolved in an isopropanol solution, and then with the SPECTROstar Nano (BMG Labtech, Germany), total cholesterol and triglycerides in blood were colorimetrically quantified at 500 nm and 550 nm, respectively, using an enzyme reagent kit (Asan Pharmaceutical Co., Ltd., Seoul, Republic of Korea).

(4) Measurement of Body Weight and Liver Weight

The body weight before drug administration and the body weight after the end of the experiment were measured. The liver weight was measured by weighing the liver extracted after lethal bleeding on the day of autopsy, and visual inspection of liver tissue was performed.

2. Results (1) Establishment of Hyperlipidemia Model

FIG. 1 illustrates liver tissues obtained by selecting one rat from each group.

Referring to FIG. 1, it can be seen that the liver of Group 4 rat administered with the pharmaceutical composition of Example 1 is the smallest among the hyperlipidemia induced groups, and the degree of lipid deposition is insignificant.

(2) Changes in Body Weight and Liver Weight

Changes in body weight and liver weight for 4 weeks including a liver weight/body weight ratio were measured for each group, and the results are shown in Table 3 below. The results were expressed as mean and standard deviation for five rats.

TABLE 3

| Classification | Liver weight (g) | | | Body weight (g) | | | Liver weight/ Body weight (%) | | |
|---|---|---|---|---|---|---|---|---|---|
| Group 1 | 16.4 | +/− | 2.0 | 496.5 | +/− | 47.8 | 3.33 | +/− | 0.54 |
| Group 2 | 26.9 | +/− | 5.5 | 582.0 | +/− | 89.7 | 4.62 | +/− | 0.56 |
| Group 3 | 24.5 | +/− | 4.5 | 571.6 | +/− | 73.9 | 4.26 | +/− | 0.32 |
| Group 4 | 23.8 | +/− | 4.1 | 577.2 | +/− | 60.1 | 4.35 | +/− | 0.31 |
| Group 5 | 23.9 | +/− | 4.2 | 576.4 | +/− | 61.3 | 4.37 | +/− | 0.33 |
| Group 6 | 23.7 | +/− | 4.0 | 577.3 | +/− | 60.8 | 4.36 | +/− | 0.34 |
| Group 7 | 24.9 | +/− | 4.1 | 578.9 | +/− | 60.9 | 4.45 | +/− | 0.31 |
| Group 8 | 25.2 | +/− | 4.3 | 579.3 | +/− | 61.1 | 4.49 | +/− | 0.32 |
| Group 9 | 25.3 | +/− | 4.2 | 579.2 | +/− | 61.0 | 4.51 | +/− | 0.31 |

Referring to Table 3, it can be seen that, as in the results shown in FIG. 1, the liver weights of Groups 4, 5 and 6 rats administered with the compositions of Examples 1, 2 and 3, respectively, among the hyperlipidemia induced groups, were the lowest, which indicates that the compositions had an inhibitory effect on hyperlipidemia.

(3) Blood Lipid Changes (TC, TG, HDL-c, and LDL-c) and Liver Lipid Changes (TC and TG)

Changes in total cholesterol (TC), triglycerides (TG), HDL-cholesterol (HDL-c) and LDL-cholesterol (LDL-c) in blood were determined.

1) Total Cholesterol in Blood (TC)

TABLE 4

| Classification | Total cholesterol concentration in blood (mg/dL) |
|---|---|
| Group 1 | 119 |
| Group 2 | 173 |
| Group 3 | 147 |
| Group 4 | 148 |
| Group 5 | 147 |
| Group 6 | 149 |
| Group 7 | 152 |
| Group 8 | 156 |
| Group 9 | 154 |

Referring to Table 4 above, it was found that the total cholesterol level decreased in the groups administered with the compositions of the Examples.

2) Triglycerides in Blood (TG)

TABLE 5

| Classification | Triglyceride concentration in blood (mg/dL) |
|---|---|
| Group 1 | 199 |
| Group 2 | 300 |
| Group 3 | 219 |
| Group 4 | 204 |
| Group 5 | 215 |
| Group 6 | 202 |
| Group 7 | 213 |
| Group 8 | 218 |
| Group 9 | 211 |

Referring to Table 5 above, it was confirmed that the amounts of triglycerides in the groups to which the compositions of the Examples was administered were most reduced, which was similar to the amount of triglycerides in the normal group, Group 1, and was more excellent than that of atorvastatin.

3) HDL-Cholesterol in Blood (HDL-c)

TABLE 6

| Classification | HDL-cholesterol concentration in blood (mg/dL) |
|---|---|
| Group 1 | 49 |
| Group 2 | 40 |
| Group 3 | 53 |
| Group 4 | 48 |
| Group 5 | 48.3 |
| Group 6 | 48.5 |
| Group 7 | 46 |
| Group 8 | 45 |
| Group 9 | 45.5 |

Referring to Table 6 above, it was confirmed that the amounts of HDL-cholesterol in blood were increased in the groups to which the compositions of the Examples were administered.

4) LDL-Cholesterol in Blood (LDL-c)

TABLE 7

| Classification | LDL-cholesterol concentration in blood (mg/dL) |
|---|---|
| Group 1 | 39 |
| Group 2 | 100 |
| Group 3 | 48 |
| Group 4 | 73 |
| Group 5 | 72 |
| Group 6 | 70.6 |
| Group 7 | 79 |
| Group 8 | 78.4 |
| Group 9 | 77 |

Referring to Table 7 above, it was confirmed that the amounts of LDL-cholesterol in blood were reduced in the groups to which the compositions of the Examples were administered.

5) Hepatic Total Cholesterol (TC)

TABLE 8

| Classification | Hepatic total cholesterol concentration (mg/dL) |
|---|---|
| Group 1 | 82 |
| Group 2 | 182 |
| Group 3 | 146 |
| Group 4 | 161 |
| Group 5 | 160.3 |
| Group 6 | 159 |
| Group 7 | 169 |
| Group 8 | 168 |
| Group 9 | 168.7 |

Referring to Table 8 above, the groups administered with the compositions of the Examples showed a decrease in the total cholesterol level in the liver.

6) Hepatic Triglycerides (TG)

TABLE 9

| Classification | Hepatic triglyceride concentration (mg/dL) |
|---|---|
| Group 1 | 124 |
| Group 2 | 211 |
| Group 3 | 197 |
| Group 4 | 189 |
| Group 5 | 182.3 |
| Group 6 | 187 |
| Group 7 | 193 |
| Group 8 | 192.5 |
| Group 9 | 192 |

Referring to Table 9 above, it was confirmed that the groups to which the compositions of the Examples were administered showed a decrease in the amount of triglycerides in the liver, and that they had more excellent effects than Group 3 to which atorvastatin was administered.

(4) Atherogenic Index (AI) and Cardiac Risk Factor (CRF)

TABLE 10

| Classification | Dosage (mg/kg/day) | Atherogenic Index (AI) | LDL/HDL | Cardiac Risk Factor (CRF) |
|---|---|---|---|---|
| Group 1 | — | 1.4 +/− 0.6 | 0.8 +/− 0.6 | 2.4 +/− 0.6 |
| Group 2 | — | 3.4 +/− 0.6 | 2.5 +/− 0.5 | 4.4 +/− 0.6 |
| Group 3 | 5 | 1.6 +/− 0.4 | 0.9 +/− 0.4 | 2.6 +/− 0.4 |
| Group 4 | 1000 | 2.1 +/− 0.4 | 1.4 +/− 0.5 | 3.1 +/− 0.4 |
| Group 5 | 1000 | 2.2 +/− 0.4 | 1.4 +/− 0.5 | 3.3 +/− 0.5 |
| Group 6 | 1000 | 2.1 +/− 0.4 | 1.6 +/− 0.4 | 3.2 +/− 0.4 |
| Group 7 | 1000 | 2.7 +/− 0.5 | 1.8 +/− 0.4 | 3.9 +/− 0.5 |
| Group 8 | 1000 | 2.6 +/− 0.4 | 1.9 +/− 0.4 | 3.8 +/− 0.4 |
| Group 9 | 1000 | 2.8 +/− 0.6 | 1.7 +/− 0.5 | 4.0 +/− 0.5 |

Referring to Table 10 above, the atherogenic index, LDL/HDL and cardiac risk factor values of the rats administered with the compositions of the Examples were smaller than those of Group 2, indicating that they have an inhibitory effect on hyperlipidemia.

What is claimed is:

1. A method for preventing or treating hyperlipidemia, comprising:
    administrating a composition consisting of a *Salvia miltiorrhiza* extract, a *Crataegus pinnatifida* extract, a *Polygonum multiflorum* extract, and a *Ligusticum chuanxiong* extract to a subject in need thereof,
    wherein the *Salvia miltiorrhiza* extract, the *Crataegus pinnatifida* extract, the *Polygonum multiflorum* extract, and the *Ligusticum chuanxiong* extract are contained in a weight ratio of 1.5 to 2:2.6 to 3:0.4 to 1:1.4 to 2.

2. The method of claim 1, which further has a fatty liver inhibiting effect.

* * * * *